United States Patent [19]

Crossett et al.

[11] Patent Number: 5,728,154
[45] Date of Patent: Mar. 17, 1998

[54] COMMUNICATION METHOD FOR IMPLANTABLE MEDICAL DEVICE

[75] Inventors: Stanley J. Crossett, Vadnais Heights; Richard A. Nazarian, Golden Valley; Michael Hamerly, Vadnais Heights, all of Minn.

[73] Assignee: Minnesota Mining and Manfacturing Company, St. Paul, Minn.

[21] Appl. No.: 610,167
[22] Filed: Feb. 29, 1996
[51] Int. Cl.$^6$ ........................................ A61F 2/22
[52] U.S. Cl. ................... 623/3; 128/899; 600/16; 607/60
[58] Field of Search .................. 128/899, 898, 128/904, 630; 623/3, 2, 66; 607/32, 30, 60; 600/16, 17

[56] References Cited

U.S. PATENT DOCUMENTS

| | | | |
|---|---|---|---|
| 4,143,661 | 3/1979 | LaForge et al. | 128/419 |
| 4,152,786 | 5/1979 | Clark et al. | 3/1.7 |
| 4,417,349 | 11/1983 | Hills et al. | 375/60 |
| 4,453,537 | 6/1984 | Spitzer | 128/1 |
| 4,561,443 | 12/1985 | Hogrefe et al. | 128/419 |
| 4,706,689 | 11/1987 | Man | 128/903 |
| 4,925,443 | 5/1990 | Heilman et al. | 600/16 |
| 4,941,201 | 7/1990 | Davis | 455/41 |
| 4,979,506 | 12/1990 | Silvian | 128/419 |

FOREIGN PATENT DOCUMENTS 0 412 422   2/1991   European Pat. Off.

OTHER PUBLICATIONS

Rosenberg et al., "In Vivo Testing of a Clinical-size Totally Implantable Artificial Heart", Assisted Circulation 4, pp. 236–248, 1995.

Snyder et al., "In Vivo Testing of a Completely Implanted Total Artificial Heart System", ASAIO Journal 1993, pp. M177–M184.

Tatsumi et al., "A Blood Pump with an Interatrial Shunt for Use as an Electrohydraulic Total Artificial Heart", ASAIO Journal 1992, pp. M425–M430.

Weiss et al., "Progress Toward a Completely Implantable Left Ventricular Assist Device at the Pennsylvania State University", Assisted Circulation 4, pp. 124–137, 1995.

Yu et al., "A Compact and Noise Free Electrohydraulic Total Artificial Heart", ASAIO Journal 1993, pp. M386–M391.

The Institute of Electrical and Electronics Engineers Inc., Case Studies in Medical Instrument Design, "Development Of A Totally Implantable Artificial Heart Concept To Implementation", pp. 95–111, 1992.

*Primary Examiner*—David Isabella
*Attorney, Agent, or Firm*—Marshall, O'Toole, Gerstein, Murray & Borun

[57] ABSTRACT

A medical assembly, such as an artificial heart assembly, adapted to be implanted within a living subject is composed of an implantable data communications interface adapted to receive an encoded data signal from a data communications interface located outside the subject at a position remote from the medical assembly. The encoded data signal is transmitted in a plurality of periodic signal bursts, which are transmitted at a first frequency to represent a first data value and a second frequency to represent of second data value. Each of the bursts comprises a plurality of signal transitions having a third frequency greater than both the first and second frequencies.

6 Claims, 7 Drawing Sheets

COMMUNICATION METHOD FOR IMPLANTABLE MEDICAL DEVICE

This patent is subject to Government Contract No. N01-HV88105 with the National Heart, Lung and Blood Institute.

BACKGROUND OF THE INVENTION

The present invention is directed to an apparatus and method for communicating with a medical assembly, such as an artificial heart assembly, that is implantable within a subject.

As defined herein, an artificial heart assembly intended to be implanted within a subject, such as an animal or human, may be a total artificial heart (TAH) intended to replace the entire heart of the subject or a ventricular assist device (VAD) intended to replace a portion of the subject's heart.

A conventional artificial heart has previously been provided with a motor to drive a pumping mechanism for pumping blood through the artificial heart. The motor has been provided with a stator and a permanent magnet rotor rotatable with respect to the stator, the rotor being connected to a coupler for translating the rotation of the rotor into linear movement of the blood pumping mechanism. The operation of the artificial heart is controlled by a controller.

Once the artificial heart is implanted within a subject, it is extremely burdensome to remove or otherwise physically access. It would be advantageous to be able to communicate with the controller of the artificial heart after it has been implanted, without having to remove or expose any portion of the artificial heart.

SUMMARY OF THE INVENTION

The invention is directed to a medical assembly, such as an artificial heart assembly, adapted to be implanted within a living subject. The medical assembly has an implantable data communications interface adapted to receive an encoded data signal from a data communications interface located outside the subject at a position remote from the medical assembly. The encoded data signal comprises a plurality of periodic signal bursts, which are transmitted at a first frequency to represent a first data value and a second frequency to represent a second data value. Each of the bursts comprises a plurality of signal transitions having a third frequency greater than both the first and second frequencies.

The implantable data communications interface includes a receiver that receives the encoded data signal from the remote data communications interface, means for generating an envelope signal from the encoded data signal, and a decoder coupled to receive the envelope signal from the generating means. The decoder includes a detector that detects which portions of the envelope signal have a frequency substantially equal to the first frequency and which portions of the envelope signal have a frequency substantially equal to the second frequency.

The decoder may comprise means for determining the number of transitions of a clock signal which occur between successive transitions of the envelope signal, such as a programmable logic device programmed as a state machine having a number of states, the programmable logic device transitioning from one of the states to another of the states at a rate which corresponds to the clock signal.

The medical assembly may also have a transmitter that transmits a second encoded data signal to the remote data communications interface. The second data signal is encoded in a different manner than the encoded data signal received by the implantable data communications interface. The second data signal may be encoded from an original data signal having a plurality of signal transitions, each of the transitions of the original data signal being represented by a phase shift in the second encoded data signal.

The invention is also directed to a method of communication between a first data communications interface implanted within a subject and a second data communications interface positioned at a remote location outside of the subject. The method includes the step of transmitting from the second data communications interface an encoded data signal in a plurality of periodic signal bursts, the signal bursts being transmitted at a first frequency to represent a first data value and a second frequency to represent of second data value. Each of the bursts comprises a plurality of signal transitions having a third frequency greater than the first and second frequencies. The method further includes the steps of receiving the encoded data signal from the second communications interface, generating an envelope signal from the encoded data signal, and decoding the envelope signal by detecting which portions of the envelope signal have a frequency substantially equal to the first frequency and which portions of the envelope signal have a frequency substantially equal to the second frequency.

These and other features and advantages of the present invention will be apparent to those of ordinary skill in the art in view of the detailed description of the preferred embodiment, which is made with reference to the drawings, a brief description of which is provided below.

DETAILED DESCRIPTION OF A PREFERRED EMBODIMENT

Figure 1:
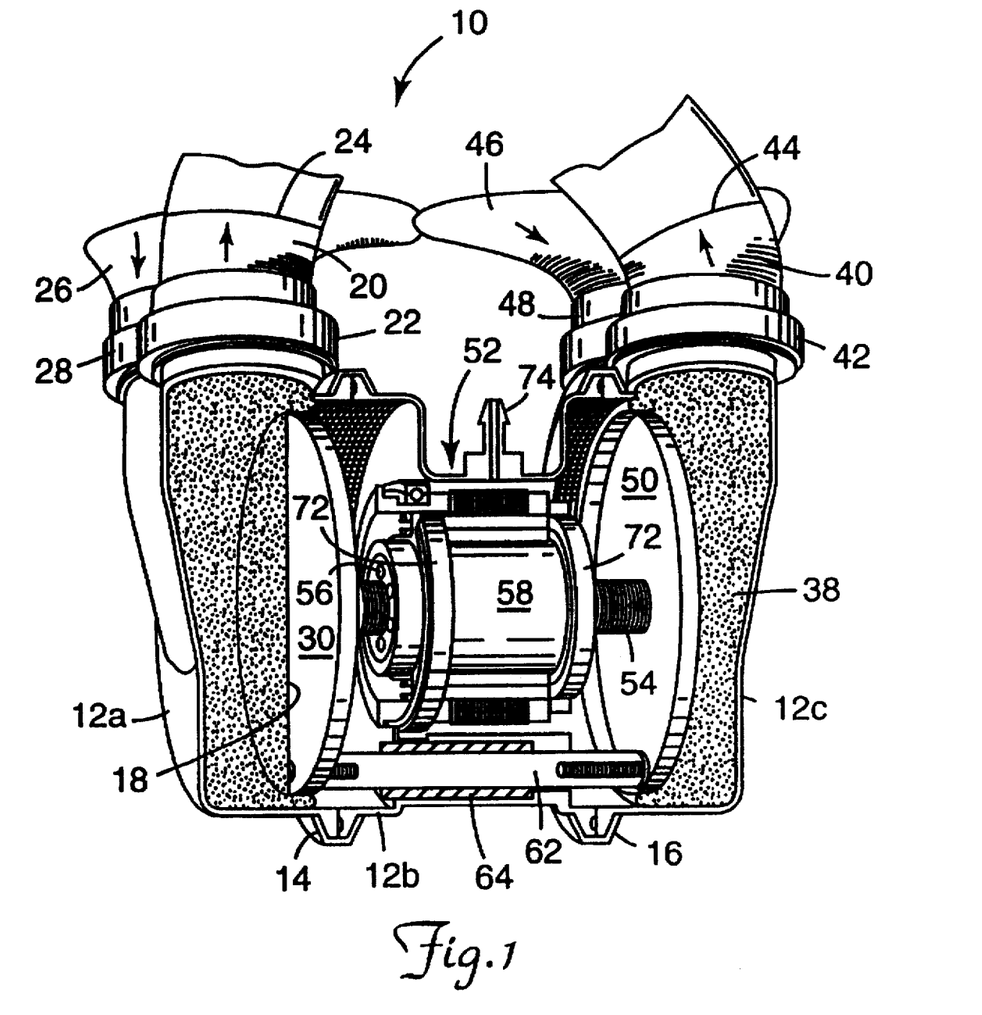
FIG. 1 is a perspective view of an implantable artificial heart, portions of which are shown in cross section.

FIG. 1 illustrates an artificial heart assembly 10 intended to be completely implanted within a subject, such as a human or an animal, to take the place of the subject's natural heart. The artificial heart 10 has a housing 12 composed of three sections 12a, 12b, 12c which are held together by a pair of annular V-rings 14, 16.

A blood reservoir within a sac 18 disposed within the housing section 12a is fluidly coupled to a blood outlet defined by an artificial vascular graft 20 connected to the housing section 12a via a threaded connector 22. The graft 20 is connected to the pulmonary artery of the subject via a suture line 24. The blood reservoir 18 is fluidly coupled to a blood inlet chamber defined by an artificial graft 26 which is connected to the housing section 12a via a threaded connector 28 and to the right atrium of the subject via a suture line (not shown). A pair of one-way check valves (not shown) are disposed in the blood inlet 26 and the blood outlet 20 to ensure that blood is pumped in the direction shown by the arrows in FIG. 1. A pusher plate 30 makes contact with and periodically deforms the blood sac 18 to force blood from the blood inlet 26 to the blood outlet 20.

A blood sac 38 disposed within the housing section 12c is fluidly coupled to a blood outlet defined by an artificial graft 40 connected to the housing section 12c via a threaded connector 42. The graft 40 is connected to the aorta of the subject via a suture line 44. The blood reservoir 38 is coupled to a blood inlet chamber defined by an artificial graft 46 which is connected to the housing section 12c via a threaded connector 48 and to the left atrium of the subject via a suture line (not shown). A pair of one-way check valves (not shown) are disposed in the blood inlet 46 and the blood outlet 40 to ensure that blood is pumped in the direction shown by the arrows. A pusher plate 50 makes contact with and periodically deforms the blood sac 38 to force blood from the blood inlet 46 to the blood outlet 40.

The pusher plates 30, 50, which form part of a pump mechanism, are driven laterally back and forth by a DC brushless motor 52 coupled to the pusher plates 30, 50 via a drive screw 54 and a coupling mechanism composed of a plurality of threaded elongate rollers 56 disposed within a cylindrical nut 58 fixed to a rotor (not shown) of the motor 52. Rotation of the rotor causes the nut 58 and rollers 56 to rotate, thus causing the drive screw 54 to be linearly displaced in a direction parallel to its longitudinal central axis. A guide rod 62 is connected between the two pusher plates 30, 50 and passes through a fixed bushing 64 to prevent the plates 30, 50 from rotating. Other mechanisms for coupling the rotor to the drive screw 54 could be used.

The rotation of the rotor is controlled via the electrical energization of a plurality of windings of a stator (not shown) which is rotatably coupled to the rotor via a pair of cylindrical bearings 72. A wire port 74 is formed in the housing section 12b to allow the passage of wires from the windings to a microcontroller 100 (FIG. 2), which may be implanted in another area of the subject, such as in the subject's abdomen.

Figure 2:
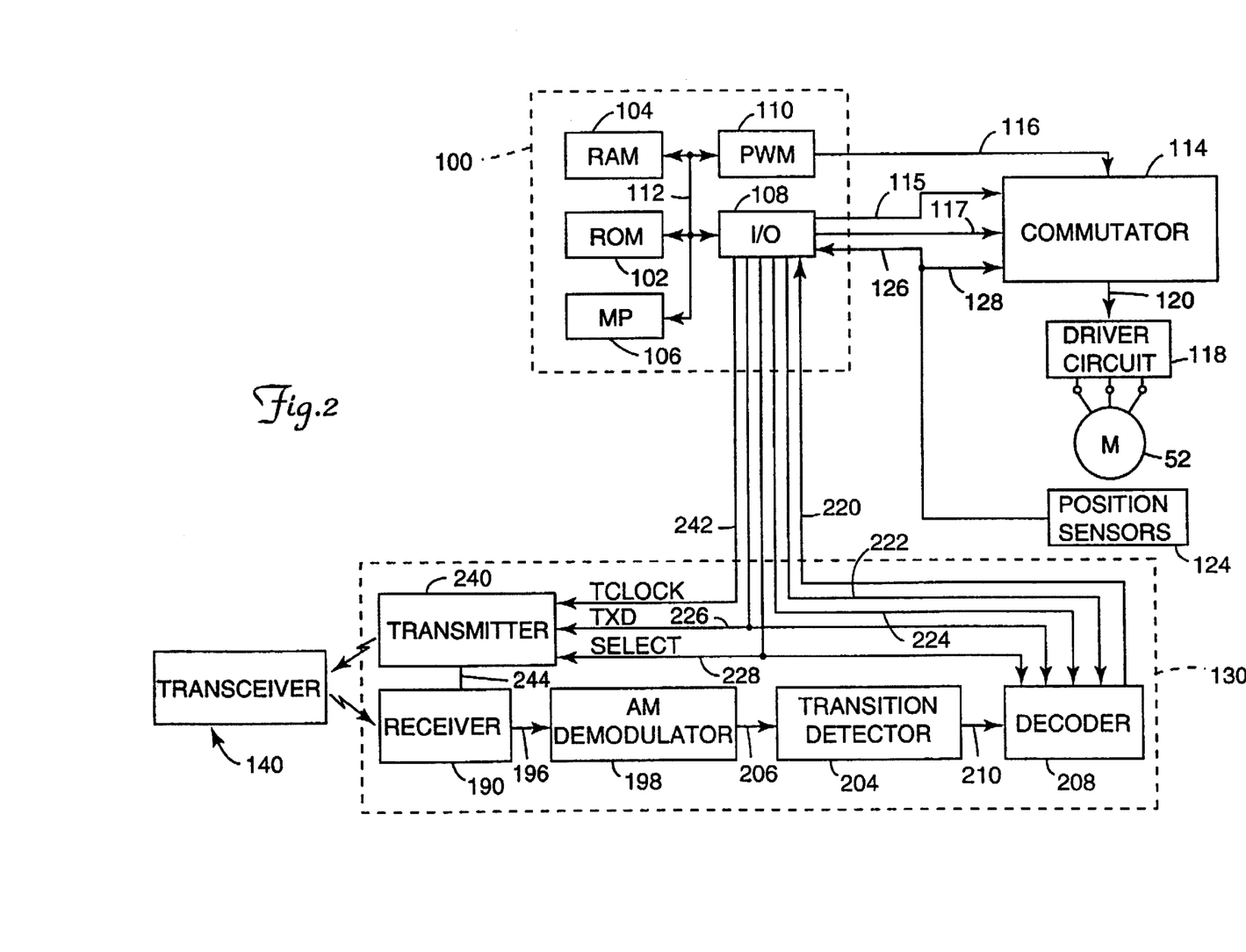
FIG. 2 is a block diagram of the electronics portion of the artificial heart of FIG. 1 and an external transceiver used to communicate with the implantable artificial heart.

Referring to FIG. 2, the controller 100, which may be a conventional integrated circuit chip, has a read-only memory (ROM) 102, a random-access memory (RAM) 104, a microprocessor (MP) 106, a conventional input/output (I/O) circuit 108, and a conventional pulse-width modulator (PWM) circuit 110, all of which are interconnected via an address and data bus 112.

The controller 100 is operatively connected to a commutator circuit 114 which periodically generates a set of commutation signals that are transmitted to a driver circuit 118 via a line 120. The driver circuit 118 generates a set of electrical drive signals that are transmitted to the stator windings of the motor 52 via three lines connected to three terminals of the motor 52.

The commutator 114 is provided with a PWM signal from the PWM circuit 110 via a line 116, a direction signal from the I/O circuit 108 via a line 115 which specifies which direction the motor 52 should be driven, and a brake signal from the I/O circuit 108 via a line 117 which may be used to apply a "brake" to the motor 52 (by shorting all of the motor terminals to ground).

Three position sensors 124, such as Hall-effect sensors, are associated with the motor 52 and generate a set of position signals that are indicative of the angular position of the rotor with respect to the stator. The position signals are transmitted to the I/O circuit 108 via a line 126 and to the commutator 114 via a line 128.

The controller 100 is connected to a data communications interface in the form of a transceiver 130 that is implanted in the subject along with the controller 100. The implanted transceiver 130 engages in two-way communication with a second transceiver 140 that is located at a remote location outside the body of the subject.

Figure 3:
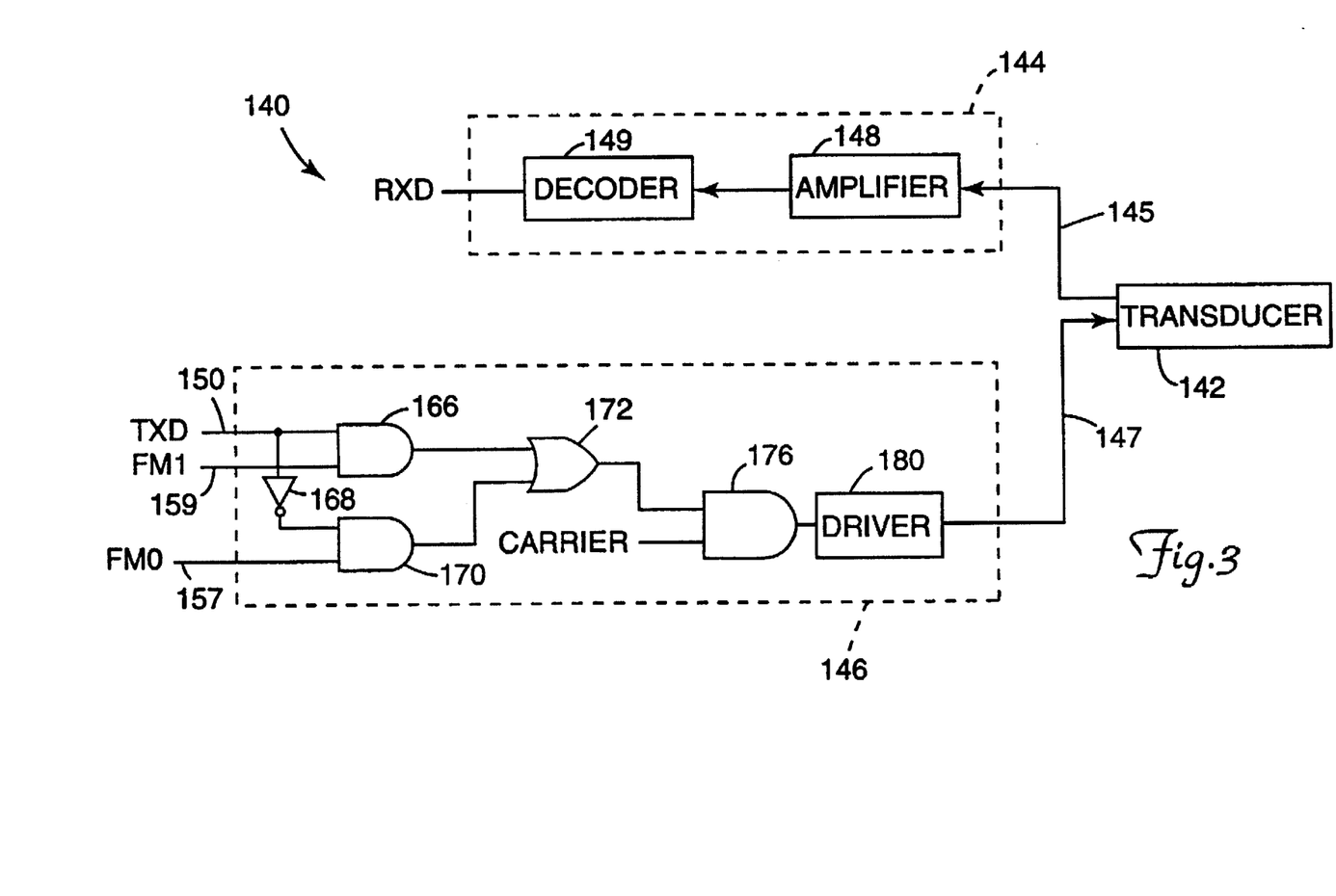
FIG. 3 is a block diagram of the external transceiver shown schematically in FIG. 2.

A block diagram of the transceiver 140 is illustrated in FIG. 3. Referring to FIG. 3, the transceiver 140 is composed of a transducer 142, such as an antenna, coupled to a receiver 144 via a line 145 and a transmitter 146 via a line 147. The receiver 144 comprises an amplifier 148 which receives incoming encoded data signals from the transducer 142 via the line 145, amplifies them, and transmits them to a conventional decoder 149, which decodes the signals as described below.

Figures 4A, 4B, 4C:
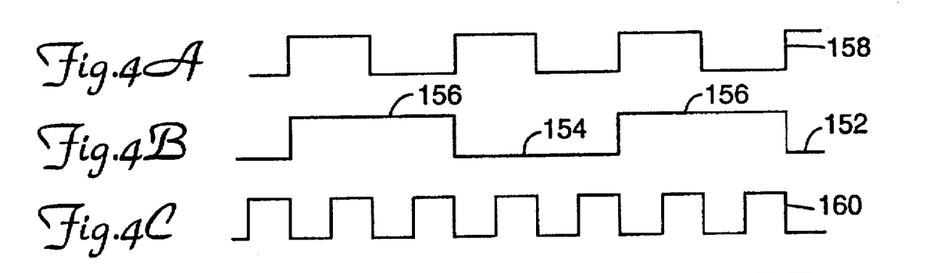
FIGS. 4A–4F illustrate a number of waveforms that are generated by the external transmitter circuit shown in FIG. 3.

The transmitter 146 acts to encode a digital data signal ("TXD") provided to it via a line 150. An exemplary portion of the TXD signal is shown as waveform 152 in FIG. 4B. Referring to FIG. 4B, the waveform 152 has a portion 154 with a relatively low voltage, such as zero volts, which represents logic "0" and two portions 156 with a relatively high voltage, such as five volts, which represent logic "1." Thus, the middle portion of the data waveform 152 shown in FIG. 4A would represent the data stream "101."

The TXD signal is transmitted at a particular data rate, such as 300 bits per second (baud). A clock signal 158 having a frequency of 300 hertz is shown in FIG. 4A. For a 300 baud data rate, the duration of each of the three signal portions 154, 156 of the data waveform 152 would be 3.3 milliseconds (ms), equal to one full cycle of the clock signal 158. Two consecutive data bits having the same value could thus be represented by a single signal portion having a constant value for 6.6 ms, equal to two full cycles of the clock signal 158. For example, the data string "11" could be represented by a 6.6 ms duration signal having a relatively high magnitude. The particular manner of encoding the data bits prior to their being provided to the transmitter 146 is not important; the present invention can be utilized for any digital data streams.

Figure 4D:
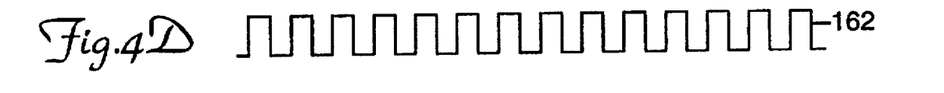

The TXD signal input to the transmitter 146 is selectively encoded via a first frequency-modulating signal FM0 generated on a line 157 by a conventional oscillator or clock circuit (not shown) and a second frequency-modulating signal FM1 generated on a line 159 by a conventional oscillator or clock circuit (not shown). An exemplary portion of the FM0 signal is shown as waveform 160 in FIG. 4C, and an exemplary portion of the FM1 signal is shown as waveform 162 in FIG. 4D. The frequency of the waveform 160 (which should be at least twice the frequency of the data waveform 152 for accurate data sampling purposes) is shown to be four times that of the data waveform 152, and the frequency of the waveform 162 is shown to be eight times that of the data waveform 152.

Referring back to FIG. 3, the TXD signal and the FM1 signal are provided to an AND gate 166. The TXD signal on the line 150 is complemented by an inverter 168, which provides the complemented TXD signal to an AND gate 170, along with the FM0 signal. The output of each of the AND gates 166, 170 is transmitted to an input of an OR gate 172.

It should be appreciated that, when the value of the TXD signal is logic "1," the output of the AND gate 166 is the FM1 signal, and the output of the AND gate 170 is a constant logic "0" (because the complemented TXD signal is logic "0"). Similarly, when the value of the TXD signal is logic "0," the output of the AND gate 166 is a constant logic "0," and the output of the AND gate 170 is the FM0 signal. Thus, at any given time, either the FM1 signal or the FM0 signal is being output by one of the AND gates 166, 170.

Figure 4E:
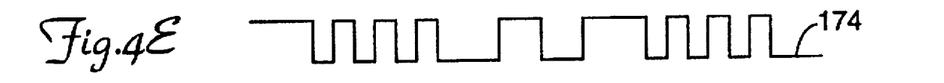

The OR gate 172 basically combines the FM0 and FM1 signal portions output by the AND gates 166, 170. FIG. 4E illustrates a waveform 174 representing the signal that would be output by the OR gate 172 for the exemplary waveforms 152, 160, 162 of FIGS. 4B–4D. It should be noted that the waveform 174 has a relatively high frequency (equal to the frequency of the waveform 162 in FIG. 4D) during each logic "1" portion 156 of the data waveform 152 and a relatively low frequency (equal to the frequency of the waveform 160 in FIG. 4C) during each logic "0" portion 154 of the data waveform 152.

Figure 4F:
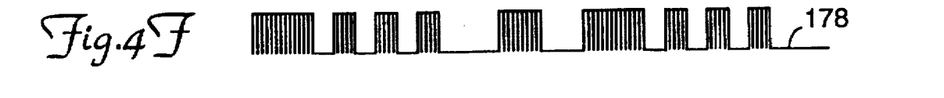

The output of the OR gate 172 just described is transmitted to an AND gate 176, along with a high frequency carrier signal generated by a conventional oscillator or clock circuit (not shown). The frequency of the carrier signal, which should be at least about ten times the frequency of the signal to be modulated, may be one megahertz, for example. The AND gate 176 generates an output signal having a shape represented by the waveform 178 shown in FIG. 4F. Referring to FIG. 4F, the waveform 178 has a high frequency in those portions which correspond to the relatively high portions of the waveform 174 of FIG. 4E and a zero value in those portions which correspond to the relatively low portions of the waveform 174 of FIG. 4E.

The output generated by the AND gate 176 is provided to a driver circuit 180, which amplifies the signal and transmits it to the transducer 142, which converts the electrical signal into a physical signal which is transmitted to a receiver 190 of the implanted transceiver 130 (FIG. 2) through the skin of the subject.

Figure 5A:
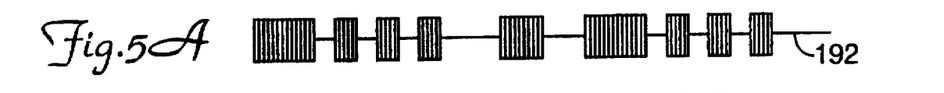
FIGS. 5A–5E illustrate a number of waveforms that are generated by the receiver portion of the implantable transceiver shown in FIG. 2.
Figure 5B:
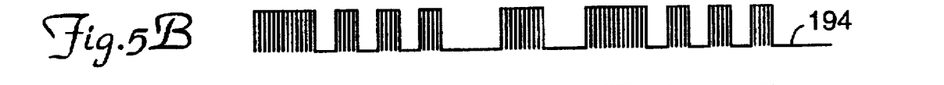
Figure 5C:
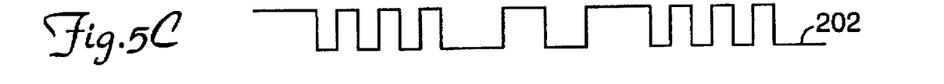

Referring to FIG. 2, the receiver 190 amplifies the signal received from the transducer 142 (FIG. 3) to generate a signal having the shape of a waveform 192 shown in FIG. 5A and rectifies the amplified signal to generate a rectified signal having the shape of a waveform 194 shown in FIG. 5B. The rectified signal is transmitted via a line 196 to an AM demodulator circuit 198 which removes the high frequency carrier signal to generate a signal having a shape that approximates the envelope of the rectified signal, the shape of which is generally shown as waveform 202 in FIG. 5C.

The output of the AM demodulator circuit 198 is transmitted to a transition detector circuit 204 via a line 206. As described below, the transition detector 204 compares the magnitude of the signal provided on the line 206 with an adaptive threshold value to determine which portions of the signal on the line 206 should be assigned a logic "0" value and which portions should be assigned a logic "1" value. The transition detector 204 outputs a frequency-modulated signal having a shape which approximates that of the waveform 202 of FIG. 5C. The difference between the shape of the output signals generated by the AM demodulator and transition detector circuits 198, 204 is that the transition detector circuit 204 generates a signal having transitions (between logic "0" and logic "1" portions) that are closer to being vertical.

The frequency-modulated signal generated by the transition detector 204 is output to a decoder circuit 208 via a line 210. The decoder 208 converts the frequency-modulated signal into a data signal having logic "0" portions which coincide with the relatively low frequency portions of the frequency-modulated signal and logic "1" portions which coincide with the relatively high frequency portions of the frequency-modulated signal. The shape of the data signal output by the decoder 208 is generally represented by a waveform 214 shown in FIG. 5D. The data signal generated by the decoder 208 is transmitted to the I/O interface 108 of the controller 100 via a line 220.

To facilitate the operation of the decoder 208, the controller 100 transmits to the decoder 208, a RESET signal via a line 222, an RCLOCK signal via a line 224, a TXD signal via a line 226, and a SELECT signal via a line 228. The TXD and SELECT signals are also provided to a transmitter 240, which allows the implanted medical assembly 10 to transmit data to the remote transceiver 140. The controller 100 provides a TCLOCK signal to the transmitter 240 via a line 242, and the transmitter 240 is connected to the receiver 190 via a line 244.

Figure 6:
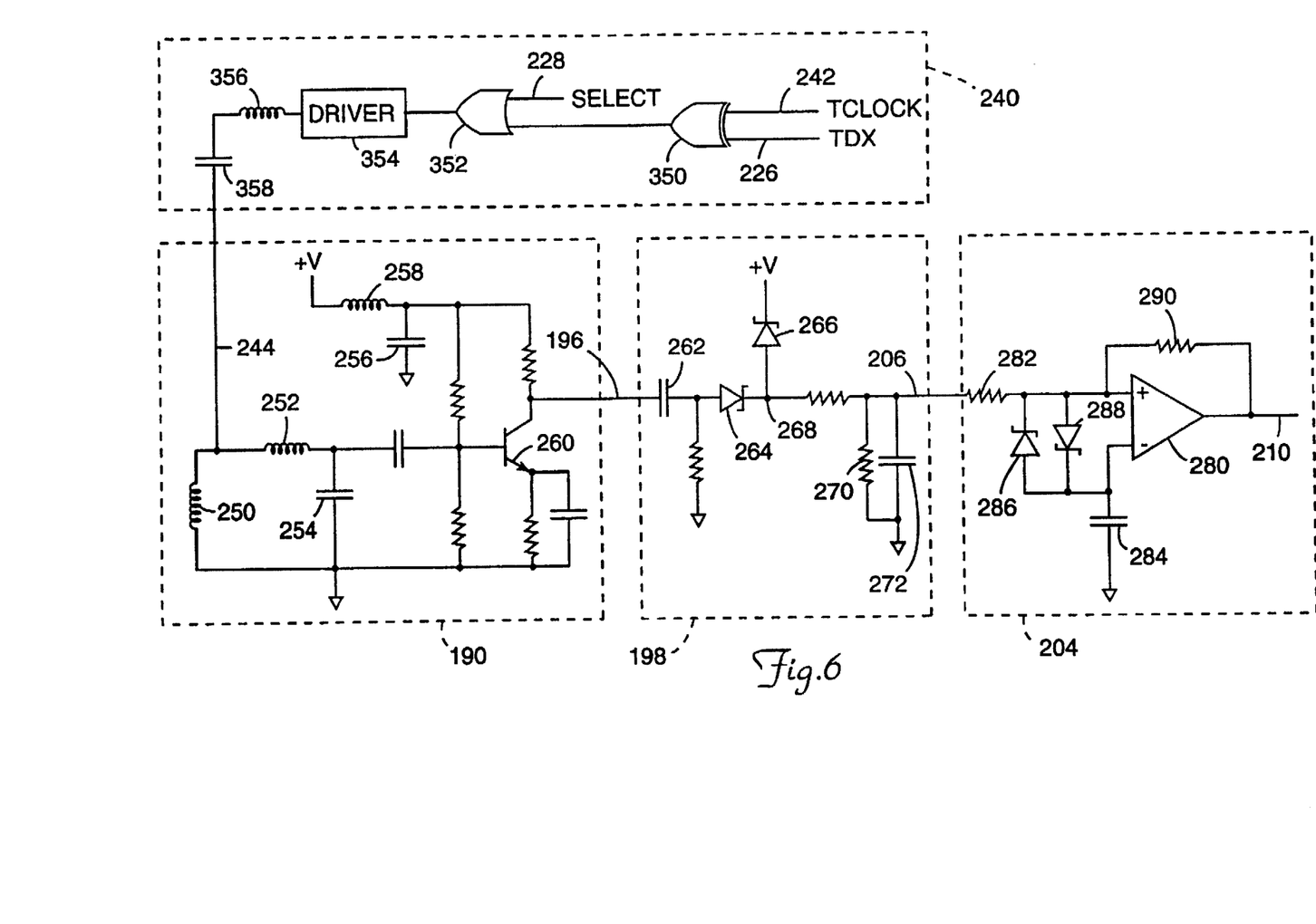
FIG. 6 is a circuit diagram of portions of the implantable transceiver shown schematically in FIG. 2.

A circuit diagram of the receiver 190, the AM demodulator circuit 198, and the transition detector 204 is shown in FIG. 6. Referring to FIG. 6, the receiver 190 has a receiver coil 250, an inductor 252, and a capacitor 254 which together have a resonant frequency tuned to receive the high frequency carrier signal transmitted by the remote transceiver 140. A capacitor 256 and an inductor 258 together form a low pass filter which filters the power supply voltage V. The receiver 190 also includes an amplifier circuit composed of a transistor 260 and associated biasing components.

The AM demodulator circuit 198 has a DC blocking capacitor 262 and a Schottky diode 264 which acts as a half-wave rectifier. A second Schottky diode 266 provides overvoltage protection by preventing the voltage at a point 268 from surpassing a predetermined voltage threshold. A resistor 270 and a capacitor 272 act as a filtering circuit to smooth out the half-wave rectified signal generated at the output of the Schottky diode 264.

The transition detector 204 includes a comparator 280 having a positive terminal which receives the rectified and filtered data signal on the line 206 and a negative terminal which is connected to a circuit, composed of a resistor 282, a capacitor 284, and two Schottky diodes 286, 288, which generates a floating threshold voltage with which the data signal is compared. The threshold voltage "floats" gradually, based on the RC time constant of the resistor 282 and the capacitor 284, to a value approximately equal to one-half the peak-to-peak amplitude of the data signal. A feedback resistor 290 may be utilized to provide hysteresis so that the data signal must change a predetermined amount above or below the floating threshold before the comparator 280 will change its output.

Figure 7:
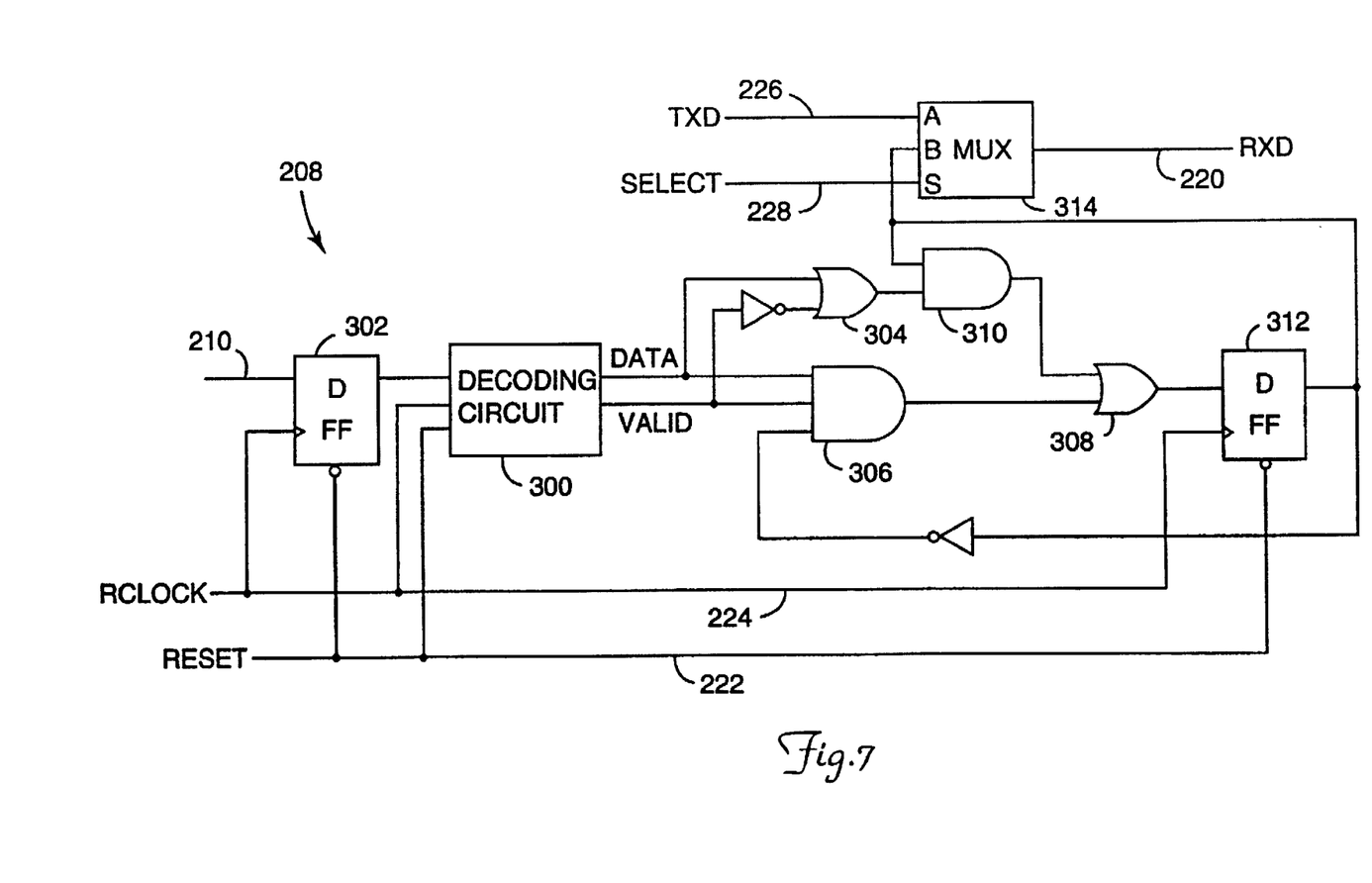
FIG. 7 is a circuit diagram of the decoder shown schematically in FIG. 2.

A circuit diagram of the decoder 208 is shown in FIG. 7. Referring to FIG. 7, the decoder 208 has a decoding circuit 300 which divides up the encoded data signal input on the line 210 into logic "0" and logic "1" portions, based upon whether portions of the data signal have a relatively high frequency or a relatively low frequency.

This is accomplished using the RCLOCK signal provided on the line 224 by the controller 100. The RCLOCK signal has a frequency that is relatively high, being a multiple of the frequencies of the FM0 and FM1 signals described above. It should be appreciated that the frequency of a particular portion of the data signal can be determined based on the number of transitions or counts of the RCLOCK signal that occur between successive changes in the data signal.

For example, assume that the frequency of the FM0 signal is 1200 Hz, the frequency of the FM1 signal is 2400 Hz, and the frequency of the RCLOCK signal is 19.2 kHz. In that case, if a portion of the encoded data signal has the FM0 frequency (which represents logic "0" as described above), for each full cycle of the encoded data signal, the RCLOCK signal will cycle eight times (since the RCLOCK signal is eight times the frequency of the FM0 signal). Similarly, if a portion of the encoded data signal has the FM1 frequency (which represents logic "1"), for each full cycle of the encoded data signal, the RCLOCK signal will cycle four times. The decoding circuit 300 detects whether a portion of the encoded data signal input via the line 210 has the FM0 frequency or the FM1 frequency by counting the number of cycles or counts of the RCLOCK signal for each full cycle of the encoded data signal.

The data decoding circuit 300 could be implemented as a conventional counter circuit connected to a simple logic circuit. The counter would have its counter input connected to receive the RCLOCK signal and its reset input connected to receive the encoded data signal, so that upon each rising and falling edge of the encoded data signal the counter would be reset and then would start counting the number of cycles of the RCLOCK signal that were received until the next rising or falling edge of the encoded data signal. The encoded data signal could then be decoded by the logic circuit in accordance with the following table.

| Clock Cycles | Data Output | Data Valid | Description |
|---|---|---|---|
| 0–2 | 0 | 0 | Noise |
| 3–6 | 1 | 1 | Data 0 |
| 7–10 | 0 | 1 | Data 1 |
| 11–15 | 0 | 0 | Noise |

Theoretically, each portion of the encoded data signal that corresponded to the FM0 frequency would generate eight clock cycles or counts for each full cycle of the encoded data signal (assuming the exemplary frequencies noted above) and each portion of the encoded data signal that corresponded to the FM1 frequency would generate four clock cycles or counts for each full cycle of the encoded data signal.

In the above table, these requirements are somewhat relaxed, and the encoded data signal is assumed to equal the FM0 frequency if the decoding circuit 300 detects between 7–10 counts of the RCLOCK signal and is assumed to equal the FM1 frequency if the decoding circuit 300 detects between 3–6 counts of the RCLOCK signal. Since the other count ranges do not correspond to either of the FM0 or FM1 frequencies, they are assumed to correspond to noise and are considered invalid data.

The decoding circuit 300 could also be provided as a conventional programmable logic device which is programmed in accordance with the state table set forth below.

| Present State | Input | Next State | Data Valid | Data |
|---|---|---|---|---|
| S0 | 0 | S0 | 0 | 0 |
| S0 | 1 | S1 | 0 | 0 |
| S1 | 0 | S0 | 0 | 0 |
| S1 | 1 | S2 | 0 | 0 |
| S2 | 0 | S0 | 0 | 0 |

-continued

| Present State | Input | Next State | Data Valid | Data |
|---|---|---|---|---|
| S2 | 1 | S3 | 0 | 0 |
| S3 | 0 | S14 | 0 | 0 |
| S3 | 1 | S4 | 0 | 0 |
| S4 | 0 | S14 | 0 | 0 |
| S4 | 1 | S5 | 0 | 0 |
| S5 | 0 | S14 | 0 | 0 |
| S5 | 1 | S6 | 0 | 0 |
| S6 | 0 | S0 | 0 | 0 |
| S6 | 1 | S7 | 0 | 0 |
| S7 | 0 | S0 | 0 | 0 |
| S7 | 1 | S8 | 0 | 0 |
| S8 | 0 | S20 | 0 | 0 |
| S8 | 1 | S9 | 0 | 0 |
| S9 | 0 | S20 | 0 | 0 |
| S9 | 1 | S10 | 0 | 0 |
| S10 | 0 | S20 | 0 | 0 |
| S10 | 1 | S11 | 0 | 0 |
| S11 | 0 | S12 | 0 | 0 |
| S11 | 1 | S11 | 0 | 0 |
| S12 | 0 | S13 | 0 | 0 |
| S12 | 1 | S11 | 0 | 0 |
| S13 | 0 | S0 | 0 | 0 |
| S13 | 1 | S11 | 0 | 0 |
| S14 | 0 | S15 | 0 | 0 |
| S14 | 1 | S1 | 0 | 0 |
| S15 | 0 | S16 | 0 | 0 |
| S15 | 1 | S1 | 0 | 0 |
| S16 | 0 | S17 | 0 | 0 |
| S16 | 1 | S19 | 1 | 1 |
| S17 | 0 | S18 | 0 | 0 |
| S17 | 1 | S19 | 1 | 1 |
| S18 | 0 | S0 | 0 | 0 |
| S18 | 1 | S19 | 1 | 1 |
| S19 | 0 | S2 | 1 | 1 |
| S19 | 1 | S2 | 1 | 1 |
| S20 | 0 | S21 | 0 | 0 |
| S20 | 1 | S1 | 0 | 0 |
| S21 | 0 | S22 | 0 | 0 |
| S21 | 1 | S1 | 0 | 0 |
| S22 | 0 | S23 | 0 | 0 |
| S22 | 1 | S1 | 0 | 0 |
| S23 | 0 | S24 | 0 | 0 |
| S23 | 1 | S1 | 0 | 0 |
| S24 | 0 | S25 | 0 | 0 |
| S24 | 1 | S1 | 0 | 0 |
| S25 | 0 | S26 | 0 | 0 |
| S25 | 1 | S1 | 0 | 0 |
| S26 | 0 | S27 | 0 | 0 |
| S26 | 1 | S1 | 0 | 0 |
| S27 | 0 | S28 | 0 | 0 |
| S27 | 1 | S30 | 1 | 0 |
| S28 | 0 | S29 | 0 | 0 |
| S28 | 1 | S30 | 1 | 0 |
| S29 | 0 | S0 | 0 | 0 |
| S29 | 1 | S30 | 1 | 0 |
| S30 | 0 | S2 | 1 | 0 |
| S30 | 1 | S2 | 1 | 0 |

As understood by those skilled in the art, a decoding circuit in accordance with the state table illustrated above would have 31 possible states, each state having a set of output values associated therewith. The circuit would transition from its present state to a particular new state, depending upon the value (logic "0" or logic "1") of the encoded data signal at each cycle of the RCLOCK signal.

Figure 8:
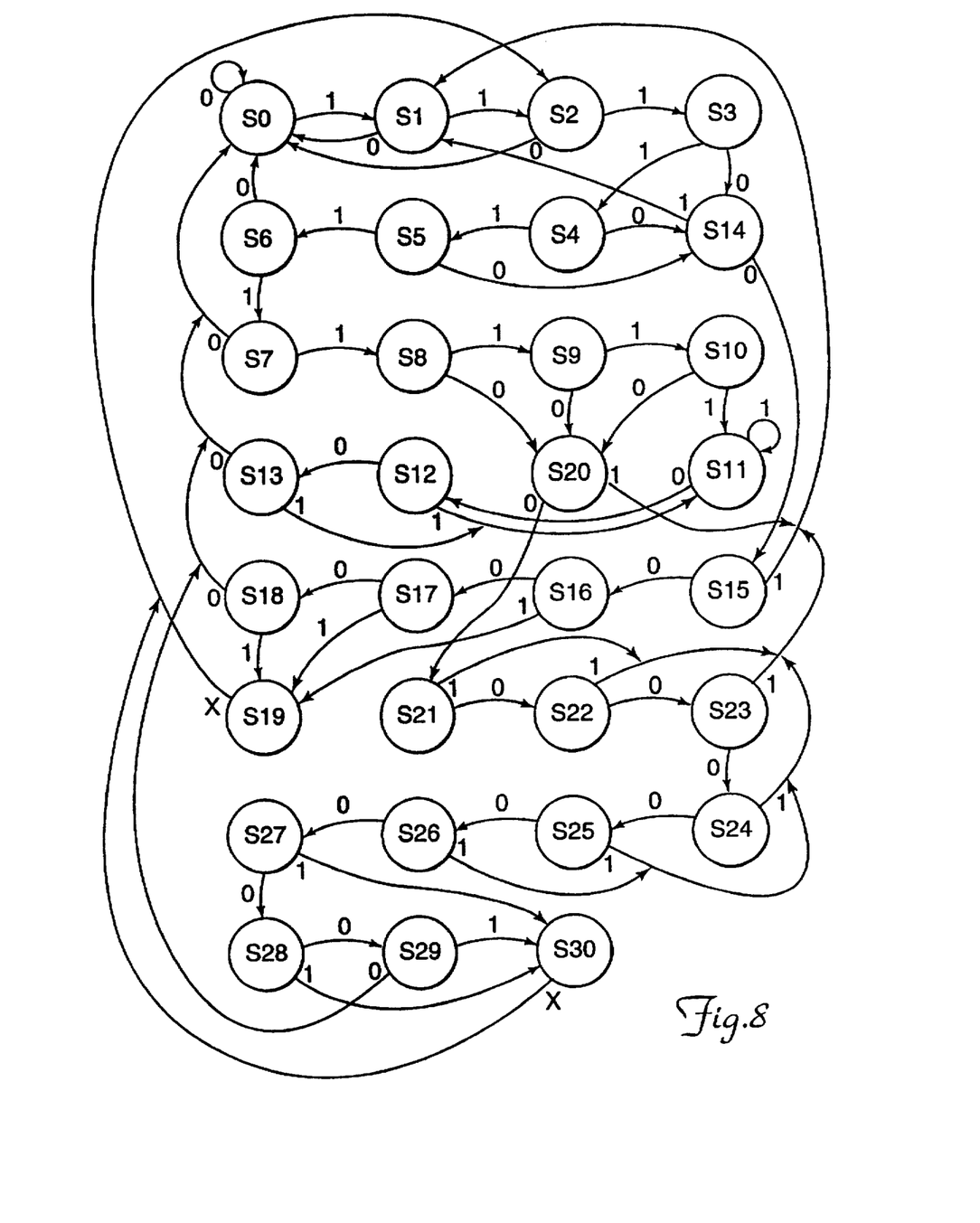
FIG. 8 is a state diagram illustrating the operation of the decoding circuit of FIG. 7.

The above table is visually represented by a state diagram shown in FIG. 8. Referring to FIG. 8, the 31 possible states are shown in the state diagram, along with the value of the encoded data signal that determines the next state. For example, when the present state is state S0 (the operation of the decoding circuit 300 begins in this state), the decoding circuit 300 will transition to state S1 if the value of the encoded data signal at the next cycle of the RCLOCK signal is logic "1" or to state S0 if the value of the encoded data signal at the next cycle of the RCLOCK signal is logic "0" (an "x" means either logic "1" or logic "0").

Before the decoding circuit 300 will recognize a valid data "1" output, the state S19 will have to be reached (see the state table set forth above; the outputs shown in the last two columns of the state table are not shown in the state diagram of FIG. 8). To reach state S19, the circuit 300 must first reach state S14. State S14 can be reached in the following three ways:

| Sequence of States | | | | | | | Input String Required | | | | | |
|---|---|---|---|---|---|---|---|---|---|---|---|---|
| S0 | S1 | S2 | S3 | S14 | | | 1 | 1 | 1 | 0 | | |
| S0 | S1 | S2 | S3 | S4 | S14 | | 1 | 1 | 1 | 1 | 0 | |
| S0 | S1 | S2 | S3 | S4 | S5 | S14 | 1 | 1 | 1 | 1 | 1 | 0 |

State S19 can be reached from state S14 in the following three ways:

| Sequence of States | | | | | | Input String Required | | | | |
|---|---|---|---|---|---|---|---|---|---|---|
| S14 | S15 | S16 | S19 | | | 0 | 0 | 1 | | |
| S14 | S15 | S16 | S17 | S19 | | 0 | 0 | 0 | 1 | |
| S14 | S15 | S16 | S17 | S18 | S19 | 0 | 0 | 0 | 0 | 1 |

Consequently, state S19 can be reached from state S0 in nine possible ways. Before a valid data "0" output is generated, the circuit 300 must reach state S30, which may be reached from state S0 in nine ways via intermediate state S20. Upon activation of the RESET signal provided on the line 222, the decoding circuit 300 resets itself, transitioning to state S0.

Referring back to FIG. 7, the decoder 208 includes a D flip-flop 302 which is used to synchronize the encoded data signal on the line 210 with the RCLOCK signal. The DATA and DATA VALID signals generated by the decoding circuit 300 in accordance with the above state tables are transmitted to a logic circuit which generates a final data signal RXD.

The logic circuit includes an OR gate 304 which receives the DATA signal and the complement of the DATA VALID signal and an AND gate 306 which receives the DATA signal and the DATA VALID signals. An OR gate 308 is connected to receive the output of the AND gate 306 and the output of an AND gate 310. The output of the OR gate 308 is provided to a D flip-flop 312 whose output, which represents the decoded data signal RXD, is transmitted to a multiplexer 314.

Generally, the logic circuit just described prevents the data output RXD from changing when invalid data is present (as determined by the value of the DATA VALID signal). In particular, if the current output of the flip-flop 312 is logic "0," then the flip-flop 312 changes to logic "1" only if the DATA and DATA VALID signals provided to the AND gate 306 are logic "1." If the current output of the flip-flop 312 is logic "1," then the flip-flop 312 changes to logic "0" only if the DATA and DATA VALID signals provided to the AND gate 306 are logic "0" and logic "1," respectively.

When data is being received by the decoder 208, the SELECT signal provided to the multiplexer 314 via the line 228 causes the RXD signal to be provided to the I/O circuit 108 via the line 220. When data is being transmitted by the implanted transceiver 130 to the remote transceiver 140, the value of the SELECT signal is changed so that the TXD signal is transmitted from the multiplexer 314 to the I/O circuit 108 via the line 220 so that the controller 100 can confirm that the TXD signal is being transmitted.

Figure 5D:
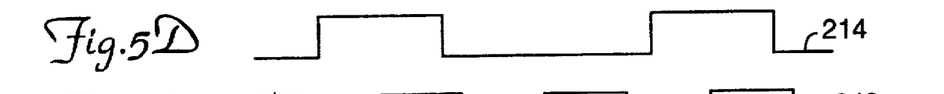
Figure 5E:
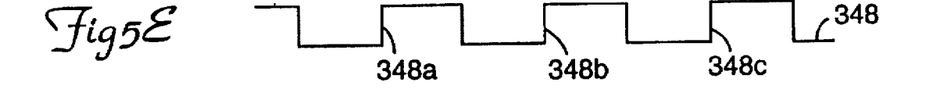

The RXD signal generated by the decoder 208 in the manner described above, the shape of which is shown in FIG. 5D as the waveform 214, is transmitted to the I/O circuit 108 (FIG. 2) via the line 220. Referring to FIGS. 5D and 5E, the I/O circuit 108, which may comprise a conventional universal asynchronous receiver/transmitter (UART) integrated circuit chip, reconstructs the data bit stream represented by the data waveform 214 based on a 300 Hz clocking signal shown in FIG. 5E as waveform 348 (corresponding to the baud rate at which the data was transmitted by the remote transceiver 140). Each data bit corresponds to the value of the data waveform 214 upon an edge of the clock waveform 348. Thus, for FIGS. 5D and 5E, the I/O circuit 108 would generate a data stream of logic "1" for the edge 348a, logic "0" for the edge 348b, and logic "1" for the edge 348c.

The implanted transceiver 130 transmits data to the remote transceiver 140 via a second data communication scheme. Referring to the circuit diagram of the transmitter 240 shown in FIG. 6, the data signal TXD generated by the controller 100 on the line 226 is provided to an EXCLUSIVE-OR gate 350 along with the TCLOCK signal on the line 242. The output of the EXCLUSIVE-OR gate 350 is provided to an OR gate 352 along with the SELECT signal on the line 228. The SELECT signal is logic "0" when the implanted transceiver 130 is transmitting data to the remote transceiver 140 and logic "1" when the transceiver 130 is receiving data from the transceiver 140. Thus, if the SELECT signal is logic "0," the output of the EXCLUSIVE-OR gate 350 is transmitted unchanged to a driver circuit 354 which amplifies the signal, which is provided to the coil 250, through an inductor 356 and a capacitor 358, which transmits the signal to the remote transceiver 140.

Figures 9A, 9B, 9C:
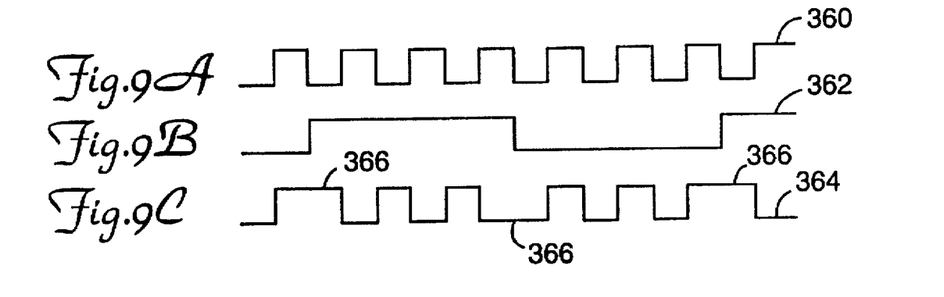
FIGS. 9A–9C illustrate a number of waveforms that are generated by the transmitter portion of the implantable transceiver shown in FIG. 2.

Referring to FIGS. 9A-9C, the shape of the TCLOCK signal is illustrated in FIG. 9A as a waveform 360, and the shape of the TXD data signal is illustrated in FIG. 9B as a waveform 362. FIG. 9C illustrates the shape of the output of the EXCLUSIVE-OR gate 350 as a waveform 364. It should be noted that when the value of the waveform 362 is logic "0," the output waveform 364 has the same shape as that of the TCLOCK waveform 360 and that when the value of the waveform 362 is logic "1," the output waveform 364 has the opposite shape as that of the TCLOCK waveform 360. It should also be noted that, for every transition of the data waveform 362, there is a 180° phase shift (coinciding with "double width" pulses 366) in the output waveform 364.

The data waveform 364 is decoded by the decoder 149 (FIG. 3) of the remote transceiver 140. The decoder 149, which may be a conventional phase locked loop circuit, detects the occurrences of the phase shifts 366 in the data waveform 364 which correspond to the transitions between logic "0" and logic "1" in the data signal. If the data stream transmitted to the remote transceiver 140 always begins with a predetermined starting string, such as "1010000" (which would be perceived by the decoder 149 as three successive transitions followed by three periods without transitions), the decoder 149 can determine the value of the data signal between each transition. Then, the data stream can be reconstructed based upon a clock signal (having a frequency corresponding to the baud rate at which the data was transmitted) in the manner described above in connection with FIGS. 5D and 5E.

Modifications and alternative embodiments of the invention will be apparent to those skilled in the art in view of the foregoing description. This description is to be construed as illustrative only, and is for the purpose of teaching those skilled in the art the best mode of carrying out the invention. The details of the structure and method may be varied substantially without departing from the spirit of the invention, and the exclusive use of all modifications which come within the scope of the appended claims is reserved.

What is claimed is:

1. A method of communication between a first data communications interface implanted within a subject and a second data communications interface positioned at a remote location outside of said subject, said method comprising the steps of:

(a) transmitting from said second data communications interface an encoded data signal in a plurality of periodic signal bursts, said signal bursts being transmitted at a first frequency to represent a first data value and a second frequency to represent of second data value, said second frequency being different than said first frequency, each of said bursts comprising a plurality of signal transitions having a third frequency, said third frequency being greater than said first frequency and greater than said second frequency;

(b) receiving said encoded data signal from said second communications interface;

(c) generating an envelope signal from said encoded data signal; and (d) decoding said envelope signal by detecting which portions of said envelope signal have a frequency substantially equal to said first frequency and which portions of said envelope signal have a frequency substantially equal to said second frequency.

2. A method as defined in claim 1 wherein said step (c) comprises the step of (e) filtering said envelope signal to remove relatively high frequency portions of said encoded data signal.

3. A method as defined in claim 1 wherein said step (d) comprises the step of determining the number of transitions of a clock signal which occur between successive transitions of said envelope signal.

4. A method as defined in claim 1 additionally comprising the steps of:

(e) encoding a second encoded data signal; and (f) transmitting said second encoded data signal to said remote data communications interface.

5. A method as defined in claim 1 additionally comprising the steps of:

(e) encoding a second encoded data signal in a different manner than said encoded data signal transmitted by said second data communications interface during said step (a); and (f) transmitting said second encoded data signal to said remote data communications interface.

6. A method as defined in claim 5 wherein said step (e) comprises the step of encoding said second encoded data signal from an original data signal having a plurality of signal transitions, each of said transitions of said original data signal being represented by a phase shift in said second encoded data signal.

* * * * *